United States Patent [19]
Shew

[11] Patent Number: 5,226,813
[45] Date of Patent: Jul. 13, 1993

[54] TOOTH REDUCTION PROCESS USING FLEXIBLE CLEARANCE TABS

[76] Inventor: W. Scott Shew, 16108 E. Peppertree, La Mirada, Calif. 90638

[21] Appl. No.: 789,318

[22] Filed: Nov. 8, 1991

[51] Int. Cl.⁵ .............................................. A61C 9/00
[52] U.S. Cl. ...................................................... 433/70
[58] Field of Search ........................................... 433/70

[56] References Cited

U.S. PATENT DOCUMENTS

| | | | |
|---|---|---|---|
| 3,126,631 | 3/1964 | McCarthy et al. | 433/70 |
| 3,421,223 | 1/1969 | Stark | 433/70 |
| 3,959,881 | 6/1976 | Kokal, Jr. | 433/70 |
| 4,547,155 | 10/1985 | Adler | 433/70 |

Primary Examiner—John J. Wilson
Attorney, Agent, or Firm—Edgar W. Averill, Jr.

[57] ABSTRACT

A flexible clearance and marking tab for facilitating the consistently accurate fitting of a dental crown. The tab is elongated, has a width about equal to the occlusal (chewing surface) of the tooth being restored and is provided in variable thicknesses between 0.5 and 2.5 millimeters. The tab is fabricated from a flexible and elastic material and has a thin marking surface on at least one of the faces which is of a color which is visible when transferred to a tooth surface. When a crown or bridge procedure is being done, the dentist uses the tab to mark high spots so that the tooth being restored can be accurately and uniformly reduced occlusally in order to provide just the right amount of clearance necessary to place the type of crown being fabricated.

1 Claim, 1 Drawing Sheet

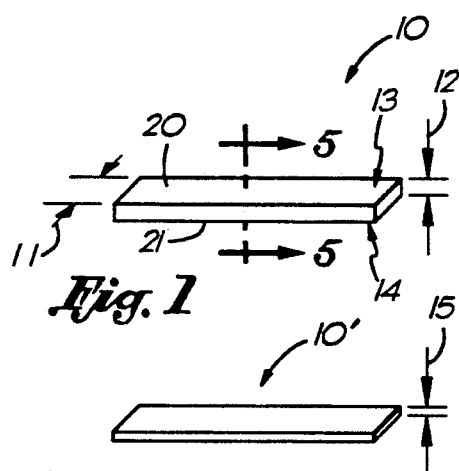
Fig. 1
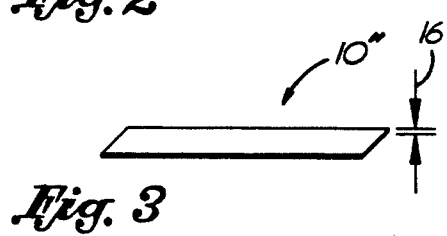
Fig. 2
Fig. 3
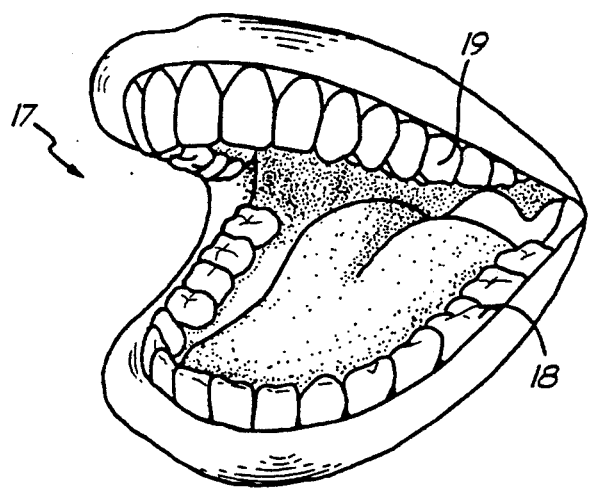
Fig. 4
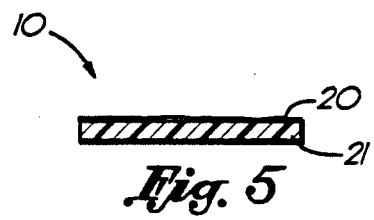
Fig. 5
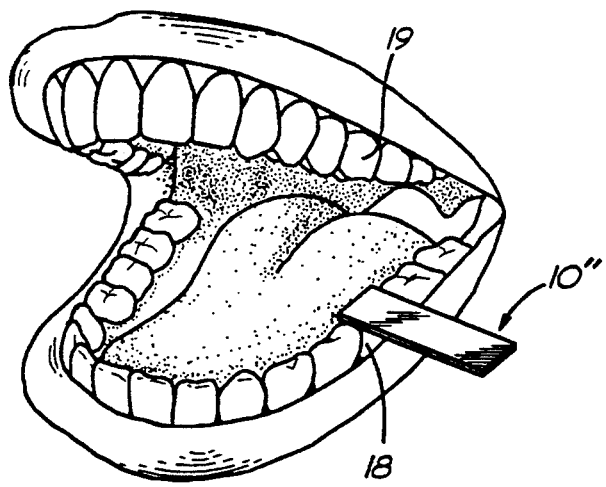
Fig. 6
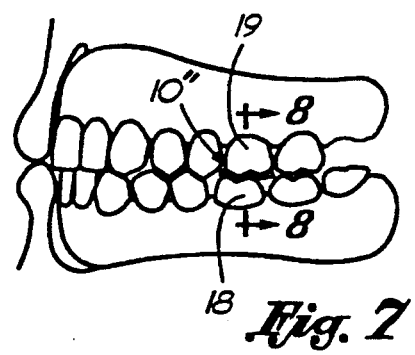
Fig. 7
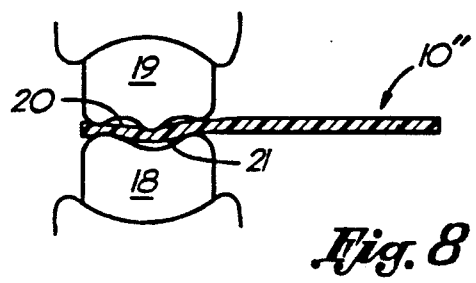
Fig. 8

TOOTH REDUCTION PROCESS USING FLEXIBLE CLEARANCE TABS

BACKGROUND OF THE INVENTION

The field of the invention is dentistry, and the invention relates more particularly to dental tools useful in preparing and fitting a tooth restoration. Dental thickness gauges of vary thicknesses are known such as that shown in U.S. Pat. No. 4,571,181. While such thickness gauges are very useful for determining whether or not the proper space has been provided below or above a tooth being restored, they fail to give any indication of where any high spots are located when sufficient clearance is not available.

Thin articulating paper is also known which is useful in determining high spots after a crown or filling has already been placed. At this point the dentist asks the patient to bite down on the articulating paper and the high spots are transferred by the rubbing of such high spots together against the articulating paper.

SUMMARY OF THE INVENTION

It is an object of the present invention to provide a device which will consistently facilitate the accurate reduction of a tooth by marking the high spots (areas that need to be reduced) before a crown is prepared for that tooth.

The present invention is for a flexible clearance and marking tab for facilitating the fitting of a crown. The tab is elongated and has about the same width as that of the chewing surface of the tooth which is being fitted. The tab is available in various thicknesses between 0.5 millimeters and 2.5 millimeters and has an upper face and a lower face. A thin marking surface is coated on at least one of the faces, and the marking surface is made of a color which is visible when placed on the surface of a tooth. The thin marking surface is sufficiently soft that a portion thereof will be transferred to a high tooth surface area when rubbed against the tooth surface under substantial pressure but will not be transferred when sufficient clearance has been achieved.

BRIEF DESCRIPTION OF THE DRAWINGS

FIG. 1 is a perspective view of a flexible clearance and marking tab of the present invention.

FIG. 2 is a perspective view of the flexible clearance and marking tab of FIG. 1 having less thickness.

FIG. 3 is a perspective view of the flexible clearance and marking tab of the present invention being yet thinner than that of FIG. 2.

FIG. 4 is a perspective view of a patient's mouth.

FIG. 5 is a cross-sectional view taken along line 5—5 of FIG. 1.

FIG. 6 is a perspective view of the patient's mouth with the flexible clearance and marking tab placed against a tooth being restored.

FIG. 7 is a side view of the patient's mouth of FIG. 6 with the jaw in a closed position.

FIG. 8 is a cross-sectional view taken along line 8—8 of FIG. 7.

DESCRIPTION OF THE PREFERRED EMBODIMENTS

A flexible clearing and marking tab is shown in perspective view in FIG. 1 and indicated by reference character 10. Tab 10 has a width 11, a thickness 12, an upper face 13 and a lower face 14. The tab of FIG. 2, indicated by reference character 10', has the same features indicated by the same reference characters as that of FIG. 1 except the thickness is indicated by reference character 15. The tab of FIG. 3 is indicated by reference character 10" and also has the same reference characters except for the thickness which is indicated by reference character 16.

The patient's jaw is shown in perspective view in FIG. 4 and indicated by reference character 17. The tooth being restored is indicated by reference character 18, and this tooth is ground down (reduced occlusally) until the space between it and the corresponding upper tooth 19 is, for instance, ½ millimeter when the jaw is fully closed as shown in FIG. 7.

The upper face 13 and the lower face 14 of each of the tabs is coated with a thin marking surface 20 and 21 respectively. The marking surface is made of a color which is visible on the surface of the tooth. The marking surface is of sufficient softness that a portion thereof will be transferred to a tooth surface when rubbed against a tooth surface under pressure but a lesser amount will be transferred when only lightly rubbed against a tooth surface, i.e., sufficient clearance has been attained. The intensity of the marking, or markings, from the carbon coating (marking surface) is directly related to the amount of pressure. Heavier pressure provides darker markings while lighter pressure causes lighter marks. A good example of a material that is appropriate for this is the coating typically used on carbon paper. This is a wax-like and carbon black coating which, of course, must be non-toxic. Either one surface or both surfaces should be coated with this marking surface. As shown in FIG. 6 tab 10" is placed so that one end of the tab overlies tooth 18 which is being prepared for a dental crown. Then, as shown in FIG. 7, the patient's jaw is closed and the tab is squeezed between tooth 18 and tooth 19. This is shown in enlarged view in FIG. 8. The patient is then asked to tap his teeth together and to slightly move his jaw side to side so that the high points between the two teeth are marked by the marking surface. The patient again opens his jaw and the high points are clearly visible to the dentist. Preferably, the tab has a width about equal to that of the chewing surface (occlusal) of the tooth being restored. The tab thickness is chosen depending upon the type of crown being placed (i.e., a full gold crown would use 0.5 or 1 millimeter thickness, whereas a porcelain crown would use 2 or 2½ millimeters of thickness). The length of the tab must be sufficient to permit the dentist to hold it securely. While a black marking surface is very effective, colors such blue or red are preferred. A rectangular shape is preferred although the corners can of course be rounded and one end may be narrowed. The tab of the present invention will enable the dentist to very accurately reduce the occlusal (chewing) surface of the tooth being restored thus preventing unnecessary over-reduction. Over-reduction can lead to retention loss of the crown being fabricated and also the possibility of nerve exposure. Under-reduction will also be eliminated. At the time of delivery, very little occlusal grinding on the newly fabricated crown will be necessary, thus eliminating perforations.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

What is claimed is:

1. A process for accurately reducing a tooth comprising the steps of:

reducing occlusally the surface of a tooth to be restored by removing at least one-half of a millimeter from the surface of the tooth to provide a reduced tooth surface;

placing an elongated tab having a thickness between 0.5 millimeters and 2.5 millimeters, which elongated tab has an upper face and a lower face, and one of said upper face or said lower face being coated with a thin marking surface which is of a color which is visible on the surface of the tooth, said marking surface being placed adjacent the reduced tooth surface; and causing the jaws of the patient to close so that said reduced tooth surface is pressed against the marking surface by an adjacent mating tooth whereby raised surfaces on the reduced tooth surface are marked by the thin marking surface.

* * * * *